United States Patent [19]

Kuhr

[11] Patent Number: 5,244,560
[45] Date of Patent: Sep. 14, 1993

[54] METHOD OF FABRICATION FOR CAPILLARY ELECTROPHORESIS AND ELECTROCHEMICAL DETECTOR FOR THE SAME

[75] Inventor: Werner G. Kuhr, Riverside, Calif.

[73] Assignee: The Regents of the University of California, Oakland, Calif.

[21] Appl. No.: 997,801

[22] Filed: Dec. 29, 1992

[51] Int. Cl.$^5$ .............. G01N 27/26; G01N 27/447; B01D 57/02
[52] U.S. Cl. ............................ 204/299 R; 204/180.1
[58] Field of Search ...................... 204/299 R, 180.1

[56] References Cited

U.S. PATENT DOCUMENTS 5,126,023 6/1992 Huang et al. ............... 204/180.1
5,169,510 12/1992 Lunte et al. ................ 204/299 R

OTHER PUBLICATIONS

Ross A. Wallingford and Andrew G. Ewing "Capillary Zone Electrophoresis with Electrochemical Detection" Analytical Chemistry, vol. 59, No. 14, (Jul. 15, 1987) 1762-1766.
Ross A. Wallingford and Andrew G. Ewing, "Capillary Zone Electrophoresis with Electrochemical Detection in 12.7 $\mu$m Diameter Columns" Analytical Chemistry vol. 60, No. 18 (Sep. 15, 1988) 1972-1975.
S. B. Khoo et al "Micellar electrokinetic capillary chromatography of vitamin $B_6$ with electrochemical detection" Journal of Chromatography, 585 (1991) 139-144.
Susan M. Lunte et al "Capillary electrophoresis with electrochemical detection employing an on-column Nafion joint" Journal of Chromatography 593 (1992) 305-312.

Primary Examiner—John Niebling
Assistant Examiner—John S. Starsiak, Jr.
Attorney, Agent, or Firm—Daniel L. Dawes

[57] ABSTRACT

An improved electrochemical detector for use in capillary zone electrophoresis having a working electrode of the order of magnitude of 32 microns in diameter inserted into a separation capillary of the order of 50 microns in diameter is fabricated as follows. The separation capillary is bonded to a rigid collar and an electrical joint through a fracture is defined in the separation capillary. The collar is telescopically disposed within a first guide capillary approximately 1.2 millimeters outer diameter. The first guide capillary is then telescopically inserted into an outer sleeve capillary of approximately 1.25 millimeters in inner diameter. Similarly a working electrode is aspirated into a drawn down second guide tube of approximately 1.2 millimeters in outer diameter. A mercury pool is disposed in the second guide tube and a contacting wire is electrically coupled to the mercury pool and hence to the working electrode. The second guide tube is then disposed within the sleeve capillary with the two guide tubes moved toward each other so that the centralized working electrode is telescopically inserted within the separation capillary. The assembly is sealed and thus serves as a rugged electrochemical detector which can be integrally fabricated on the end of a separation column.

20 Claims, 1 Drawing Sheet

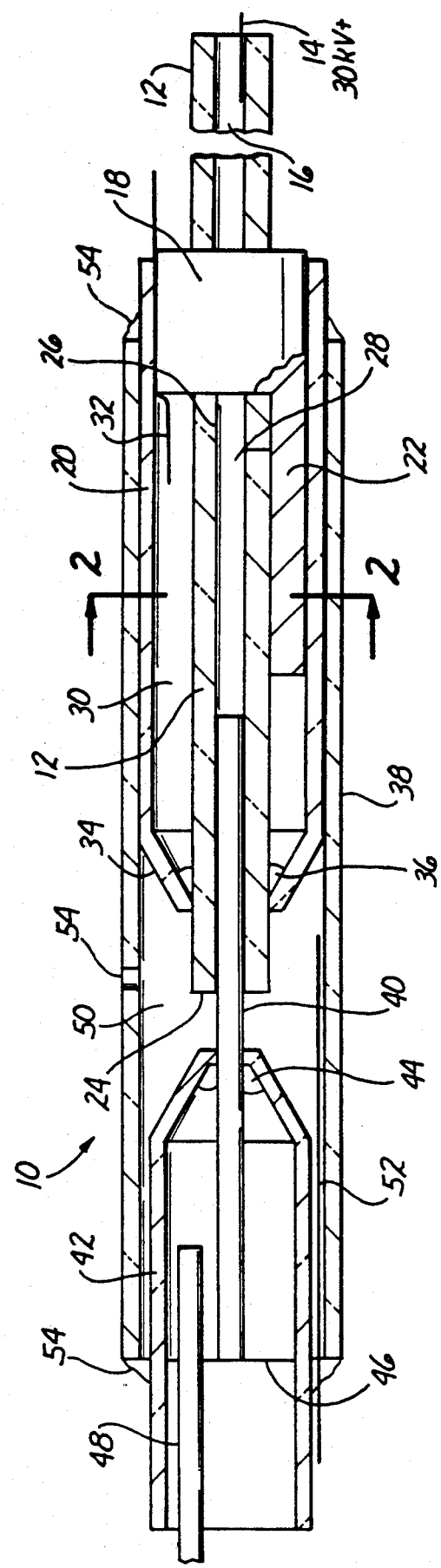
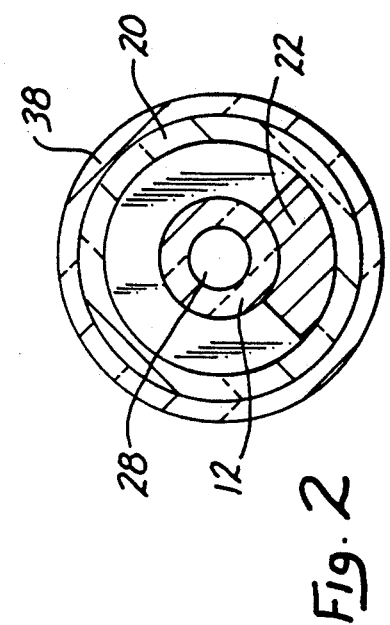

ME THOD OF FABRICATION FOR CAPILLARY ELECTROPHORESIS AND ELECTROCHEMICAL DETECTOR FOR THE SAME

BACKGROUND OF THE INVENTION

1. Field of the Invention

The invention relates to the field of electrochemical detectors for capillary electrophoresis, and more particularly to a method for fabricating such detectors and the resulting structure realized from the fabrication techniques.

2. Description of the Prior Art

In simplified terms, capillary zone electrophoresis is the separation of a chemical material along the length of a capillary column filled with a buffered or neutral solution. By the application of a high DC voltage, typically in the order of 30,000 volts, materials in an unknown sample are driven from the positive anode toward a negative anode at the detector end of the column at varying rates. As these charged constituents reach the detector near or at the grounded anode of the electrophoresis column, small signals are detected. The time of arrival of the constituent is indicative of the type of material and is used for qualitative analysis. The amplitude of the detected signal can be calibrated against standardized samples to measure the amount of material or its concentration within the sample.

The particular advantage of capillary zone electrophoresis is the very small amount of sample that is needed in order to obtain an electrochemical signal. Typically, the samples measure in the range of nanoliters and practitioners in the art have achieved capillary electrophoresis with samples of the order of picoliters, which approaches the size of many constituents within a single living cell.

Capillary zone electrophoresis is a powerful separation technique which is ideally suited for the analysis of charged species or materials. See J. W. Jorgenson, ACS Symposium Series 335, pages 182-198 (1987). One of the major limitations with capillary zone electrophoresis, however, is related to detection in the eluted zone. See J. W. Jorgenson et al., Science, 222, pages 266-72 (1983). Since small diameter capillaries, typically with an inner diameter of less than 75 microns, are required for efficient separation, detection of the sample must be made in the capillary column itself. Many different types of detection strategies have been implemented in capillary zone electrophoresis, see for example the review of R. Wallingford et al., Advances in Chromatography Series, 29, pp 1-76 (1989). The most sensitive techniques found to date involve laser induced fluorescence, see P. Gozel, Anal. Chem., 59, pages 44-9 (1987); D. E. Burton et al., Chromatogr. Sci. 24, pages 347-51 (1986); and W. G. Kuhr et al., Anal. Chem. 60, pp 1832-4 (1988) and involve electrochemical detections, see R. A. Wallingford et al., Anal. Chem. 60, pages 258-63 (1988); and R. A. Wallingford et al., Anal. Chem. 59, 678-81 (1987). Attomole detection limits, i.e. $10^{-18}$ injected mole of sample, have been demonstrated with these techniques, but only a few chemical species have sufficient fluorescent efficiency or electrochemical activity to enable full utilization of these types of detectors. See W. G. Kuhr, Anal. Chem. 62, pp R403-14 (1988); and R. Wallingford et al., Anal. Chem. 60, 1972-75 (1988).

Electrochemical detection has been shown to have virtually the same level of sensitivity when used with capillary zone electrophoresis, but electrochemical detection is much less expensive to perform and has more general applications. Extremely sensitive electrochemical measurements can be made using capillary zone electrophoresis by electrically decoupling an amperometric detector from the electrophoretic power supply. See R. Wallingford et al., Anal. Chem., 59, 1962-66 (1987). According to this art, a small break in the separation capillary several centimeters before the detector acts as an electrically conductive joint to remove current from the separation column without disturbing the flow of the fluid buffer along the capillary column. In this technique, a carbon fiber typically with a radius of 5 to 10 microns and 100 to 500 microns in length is inserted into the end of the capillary column with the reference electrode placed in the buffer solution at the end of the capillary. By this combination, an amperometric detector with a volume of only of the order of a few tens of picoliters is provided. Careful matching of the outer diameter of the carbon electrode fiber with the inner diameter of the capillary allows nanomolar detection limits to be easily obtained for indoles, catecholamines and their metabolites.

One of the major problems with a detector as just described arises in the fabrication of the capillary tube relative to the carbon fiber electrode. A very small electrical joint with a width of less the 1 micron must be introduced into the separation column and the two segments of the capillary must remain perfectly aligned to allow the flow of the analyte to continue uninterruptedly along the capillary column to the detector. In addition, insertion of the carbon fiber into the separation capillary is performed using micromanipulators which are expensive and delicate mechanical devices requiring considerable talent and finesse for their successful operation. Further, electrophoretic columns using micromanipulators have a design such that their use with vacuum injection systems, which can be very helpful in filling and purging the capillary column, is very difficult if not impossible.

Therefore, what is needed is some type of capillary zone electrophoresis which can be deployed in the separation column and achieve high levels of sensitivity of electrochemical detection without the need or difficulty of using micromanipulators, and further which is rugged in its design such that critical misalignment of the capillary in the fiber cannot occur under normal handling and use.

BRIEF SUMMARY OF THE INVENTION

The invention is a method for fabrication of an electrochemical detector for use in capillary zone electrophoresis. The method of fabrication comprising the steps of telescopically disposing the end of a separation capillary column into a first guide tube to centralize the end within the guide tube. The end of the separation capillary column may if desired be fixed to the first guide tube. The end of the separation capillary column and the first guide tube is telescopically disposed within an outer sleeve to centralize the end and first guide tube within the outer sleeve. A working electrode is telescopically disposed into a second guide tube to centralize the working electrode within the second guide tube. The second guide tube is telescopically disposed within the outer sleeve to centralize the working electrode and second guide tube within the outer sleeve. The first and second guide tubes are disposed toward each other to insert the working electrode within the end of the separation capillary tube by a predetermined distance. As a result, an electrochemical detector is formed on the end of the separation capillary without the use of micromanipulation.

The step of telescopically disposing the separation capillary tube into the first guide tube comprises the step of telescopically disposing the separation capillary tube into a rigid collar and then telescopically disposing the rigid collar into the first guide tube.

The step of telescopically disposing the separation capillary tube into the rigid collar further comprises the step of fixing the separation capillary tube to the rigid collar and forming an electrical joint to permit electrical conduction of current from the interior of the separation capillary tube to the exterior of the separation capillary tube.

The separation capillary tube is comprised of friable glass and the step of forming the electrical joint is comprised of the step of creating a fracture in the glass separation capillary tube while the tube is fixed to the rigid collar.

The method further comprises the step of fixing the first and second guide tubes to the outer sleeve to form an integral detector unit. The separation capillary tube is integral with an electrophoresis column, and each of the steps is performed with respect to one end of the column so that an integral detector in the electrophoresis column is provided.

The invention is also characterized as an electrochemical detector for use in capillary zone electrophoresis comprising an outer sleeve, and a first and second guide tube. The first guide tube is telescopically disposed in one end of the outer sleeve. The second guide tube is telescopically disposed in an opposing end of the outer sleeve. A separation capillary is telescopically disposed within the first guide tube to centralize the separation capillary within the outer sleeve. An electrode is telescopically disposed within the second guide tube to centralize the electrode within the outer sleeve. The first and second guide tubes are disposed with respect to each other such that the electrode is concentrically disposed within the separation capillary by a predetermined distance. As a result, a detector is provided which is rugged, can be fabricated without micromanipulation, and is maintained in position without the need for micromanipulative adjustment.

The detector further comprises a rigid collar telescopically disposed around the separation capillary which is concentrically disposed therethrough. The rigid collar is telescopically disposed within the first guide tube. The separation capillary is fixed to the collar and has an electrical joint defined therethrough to provide an electrical conduction path between the interior of the separation capillary and the interior of the first guide tube. The detector further comprises a ground electrode disposed within the first guide tube.

In one embodiment the collar is conductive and is electrically coupled through the electrical joint in the separation capillary to serve as a ground electrode. In another embodiment a ground electrode is disposed within the first guide tube.

The detector further comprises a reference electrode disposed within the outer sleeve exterior to the first and second guide tubes and electrically communicating with that portion within the outer sleeve which is in direct electrical communication with the working electrode.

The detector further comprises a mercury pool disposed in the second guide tube. The working electrode is disposed within the second guide tube in the mercury pool retained within the second guide tube. A contacting wire is disposed in the mercury pool in electrical communication therethrough with the working electrode.

The detector further comprises a passage or port for communicating with the interior of the outer sleeve exterior to the first and second guide tubes and the separation capillary so that a buffer fluid may be flowed within the outer sleeve and separation capillary.

In the preferred embodiment the first guide tube is fixed to the separation capillary. The second guide tube is fixed to the working electrode.

The invention is still further characterized as a method of disposing a cylindrical electrode into the end of a capillary tube comprising the steps of:
telescopically centralizing the cylindrical electrode within a first guide tube;
telescopically centralizing the capillary tube within a second guide tube;
telescopically disposing the first and second guide tubes within an outer sleeve and disposing the first and second guide tubes telescopically within the outer sleeve to insert the cylindrical electrode within the capillary tube by a predetermined distance.

The first guide tube is a glass capillary tube and the step of telescopically centralizing the cylindrical electrode within the first guide tube comprises the step of heating and drawing down the capillary tube around the cylindrical electrode.

The second guide tube is glass capillary tube and the step of telescopically centralizing the capillary tube within the second guide tube comprises the steps of drawing the second guide tube into a narrow capillary tip and breaking the narrow capillary tip at a position where the inner diameter of the narrow capillary tip provides a slip-fit for the capillary tube.

The method further comprises the step of fixing the capillary tube and cylindrical electrode to the first and second guide tubes respectively prior to the step of disposing the cylindrical electrode within the capillary tube by a predetermined distance.

The invention may be better visualized by turning to the following drawings.

BRIEF DESCRIPTION OF THE DRAWINGS

FIG. 1 is a simplified cross-sectional view in enlarged scale showing the assembled electrochemical detector for use with capillary electrophoresis of the invention.

FIG. 2 is a cross-sectional view of the detector of FIG. 1 taken along section lines 2—2 of FIG. 1.

The invention and its various embodiments may now be better understood by turning to the following detailed description.

DETAILED DESCRIPTION OF THE PREFERRED EMBODIMENTS

An improved electrochemical detector for use in capillary zone electrophoresis having a working electrode of the order of magnitude of 32 microns in diameter inserted into a separation capillary of the order of 50 microns in diameter is fabricated as follows. The separation capillary is bonded to a rigid collar and an electrical joint through a fracture is defined in the separation capillary. The collar is telescopically disposed within a first guide capillary approximately 1.2 millimeters outer diameter. The first guide capillary is then telescopically inserted into an outer sleeve capillary of approximately 1.25 millimeters in inner diameter. Similarly a working electrode is aspirated into a drawn down second guide tube of approximately 1.2 millimeters in outer diameter. A mercury pool is disposed in the second guide tube and a contacting wire is electrically coupled to the mercury pool and hence to the working electrode. The second guide tube is then disposed within the sleeve capillary with the two guide tubes moved toward each other so that the centralized working electrode is telescopically inserted within the separation capillary. The assembly is sealed and thus serves as a rugged electrochemical detector which can be intregally fabricated on the end of a separation column R.

FIG. 1 is a simplified cross-sectional view of a portion of the capillary zone electrophoresis column which includes a detector, generally denoted by reference numeral 10. Electrophoretic column 12, shown in broken view, is provided at one end with a high positive potential electrode 14, typically coupled to a 30 Kilovolt positive voltage supply. Separation capillary 12 is filled with a neutral buffer solution 16 which is typically a 1 to 0.1 molar potassium chloride or sodium chloride aqueous solution. In the illustrated embodiment, detector 10 and column 12 are comprised of a single integral column having an overall length of approximately 1 meter although it is expressly contemplated that detector 10 may be a separate section fitted to a capillary column of virtually arbitrary length.

The end of column 12 is fitted as it enters detector 10 into a rigid collar 18 which acts in combination with capillary guide tube 20 to centralize separation capillary 12 in capillary guide tube 20. In the illustrated embodiment, separation capillary 12 is a fused silica capillary while collar 18 is a 24 gauge hypodermic needle which has been ground flat on its distal end to define a supporting lip 22, best depicted in FIG. 2, to which capillary guide tube 20 is epoxied or otherwise fixed.

At a predetermined distance away from end 24 of separation capillary 12, separation capillary 12 is fractured to form a fracture or break 26 which extends generally circumferentially around and through the entire body of separation capillary 12. The bonding of separation capillary 12 to section 22, however, maintains separation capillary 12 intact although fracture 26 now becomes an electrically conductive pathway between interior 28 of separation capillary 12 and exterior region 30.

Collar 18 may be electrically grounded and used as the opposing pole of the electrophoretic column or alternatively a platinum or silver/silver chloride wire electrode 32 can be inserted into region 30 to serve at the ground electrode. Collar 18 is telescopically inserted into a second capillary tube 20, which in the illustrated embodiment is 1.2 millimeter outer diameter, fused silica, capillary tube. Heating and drawing the glass of capillary guide tube 20 down to the diameter only slightly larger than separation capillary 12 causes end 34 of capillary tube 20 to be drawn down during its formation to a inner diameter almost equal to the outer diameter of separation capillary 12. An epoxy 36 is disposed around the joint between separation capillary 12 and necked-down portion 34 to seal their connection.

The assembly of collar 18, separation capillary 12 and telescopically disposed capillary guide tube 20 are then placed within a third capillary outer sleeve 38 which in the illustrated embodiment is a 1.25 millimeter inner diameter, fused-silica, capillary tube. Thus the method of fabrication to this point is comprised of the steps of providing a flattened collar 18 to which separation capillary 12 is bonded with fracture 26 then being formed in the bonded section. Collar 18 together with electrode 32 are then inserted with separation capillary 12 into second capillary guide tube 20. The neck-down portion 34 of capillary guide tube 20 is then bonded to the adjacent surface of separation capillary 12. This subassembly is then inserted into third capillary outer sleeve 38 and the right hand portion of the device is completed as shown in FIG. 1. Region 30 between capillaries 12 and 20 is intended to be filled when in use with a 1 molar potassium chloride solution to provide a neutral buffer electrolyte. The steps of fabrication need not be practiced in the order just described as long as the resulting structure shown in FIG. 1 is the ultimate result.

In the illustrated embodiment, the working electrode of detector 10 is a carbon fiber microelectrode 40 formed by aspirating a 32 micron outside diameter carbon fiber into guide tube 42 and then heating and drawing the glass down to the diameter only slightly larger than electrode 40. Electrode 40, as before, is then sealed to guide tube 42 by means of epoxy 44 applied to their juxtapositioned surfaces. Electrical connection is made to electrode 40 by providing in the end of guide tube 42 a pool of mercury 46 into which a contacting wire 48 is disposed. Outer glass tube 38 is intended to be filled with a neutral buffer, filling region 50 and second guide tube 42 with its assembled electrode 40 inserted into the end of outer sleeve 38. Outer sleeve 38 has an inner diameter only slightly larger than the outer diameter of capillary guide tubes 42 and 20. Therefore, as the electrode assembly shown in the left of FIG. 1 is moved toward the right in FIG. 1, carbon fiber 40 is automatically and accurately aligned along the center of outer sleeve 38 and hence separation capillary 12. Electrode 40 is then be inserted by any selected amount into the end of separation capillary 12 and into capillary space 28. The carbon fiber is easily guided into separation capillary space 28, in the illustrated embodiment to a depth of about 500 microns, without the use of a micromanipulator. In addition, and platinum or silver/silver chloride reference electrode 52 is disposed in space 50 to be used as part of the sensing electrode system.

The assembled detector as shown in FIG. 1 is then cemented into place using epoxy 54 with result that a rugged, sealed, electrochemical detector has been made in a manner which is integral with the separation column. Electrodes 52 and contacting wire 48 are then coupled to a conventional high sensitivity potentiostat such as is capable of making current measurements with 100 femtoamperes of RMS noise or less and with an RC time constant of 1-10 Hertz.

If desired, space 50 within outer sleeve 38 may have a hole defined therethrough so that buffer solution may be communicated with it and flowed through the space. A very slight gap of approximately 50-100 microns exists between electrode 40 and the inner diameter of capillary tube 12 so that separation capillary 12 may be vacuum filled to inject samples or the neutral solution within the electrophoretic column changed. It is a further advantage of the detector of the invention that it has a structure which is also compatible with the simultaneous use of conventional ultraviolet or florescence detectors.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. A method for fabrication of an electrochemical detector for use in capillary zone electrophoresis comprising the steps of:
   telescopically disposing the end of a separation capillary column into a first guide tube to centralize said end within said guide tube;
   fixing said end of said separation capillary column to said first guide tube;
   telescopically disposing said end and said first guide tube within an outer sleeve to centralize said end and first guide tube within said outer sleeve;
   telescopically disposing a working electrode into a second guide tube to centralize said working electrode within said second guide tube;
   telescopically disposing said second guide tube within said outer sleeve to centralize said working electrode and second guide tube within said outer sleeve; and
   disposing said first and second guide tubes toward each other to insert said working electrode within said end of said separation capillary tube by a predetermined distance,
   whereby an electrochemical detector is formed on said end of said separation capillary without the use of micromanipulation.

2. The method of claim 1 where said step of telescopically disposing said separation capillary tube into said first guide tube comprises the step of telescopically disposing said separation capillary tube into a rigid collar and then telescopically disposing said rigid collar into said first guide tube.

3. The method of claim 2 where said step of telescopically disposing said separation capillary tube into said rigid collar further comprises the step of fixing said separation capillary tube to said rigid collar and forming an electrical joint to permit electrical conduction of current from the interior of said separation capillary tube to the exterior of said separation capillary tube.

4. The method of claim 3 wherein said separation capillary tube is comprised of friable glass and the step of forming said electrical joint is comprised of the step of creating a fracture in said glass separation capillary tube while said tube is fixed to said rigid collar.

5. The method of claim 1 further comprising the step of fixing said first and second guide tubes to said outer sleeve to form an integral detector unit.

6. The method of claim 1 wherein said separation capillary tube is integral with an electrophoresis column, each of said steps being performed with respect to one end of said column so that an integral detector in said electrophoresis column is provided.

7. An electrochemical detector for use in capillary zone electrophoresis comprising:
   an outer sleeve;
   a first guide tube telescopically disposed in one end of said outer sleeve;
   a second guide tube telescopically disposed in an opposing end of said outer sleeve;
   a separation capillary telescopically disposed within said first guide tube to centralize said separation capillary within said outer sleeve; and
   an electrode telescopically disposed within said second guide tube to centralize said electrode within said outer sleeve, said first and second guide tubes being disposed with respect to each other such that said electrode is concentrically disposed within said separation capillary by a predetermined distance,
   whereby a detector is provided which is rugged, can be fabricated without micromanipulation, and is maintained in position without the need for micromanipulative adjustment.

8. The detector of claim 7 further comprising a rigid collar telescopically disposed around said separation capillary concentrically disposed therethrough, said rigid collar being telescopically disposed within said first guide tube, said separation capillary being fixed to said collar and having an electrical joint defined therethrough to provide an electrical conduction path between the interior of said separation capillary and the interior of said first guide tube.

9. The detector of claim 8 further comprising a ground electrode disposed within said first guide tube.

10. The detector of claim 8 wherein said collar is conductive and is electrically coupled through said electrical joint in said separation capillary to serve as a ground electrode.

11. The detector of claim 7 further comprising a ground electrode disposed within said first guide tube.

12. The detector of claim 7 further comprising a reference electrode disposed within said outer sleeve exterior to said first and second guide tubes and electrically communicating with that portion within said outer sleeve which is in direct electrical communication with said working electrode.

13. The detector of claim 7 further comprising:
   a mercury pool disposed in said second guide tube and wherein said working electrode is disposed within said second guide tube in said mercury pool retained within said second guide tube; and
   a contacting wire disposed in said mercury pool in electrical communication therethrough with said working electrode.

14. The detector of claim 7 further comprising means for communicating with the interior of said outer sleeve exterior to said first and second guide tubes and said separation capillary so that a buffer fluid may be flowed within said outer sleeve and separation capillary.

15. The detector of claim 7 wherein said first guide tube is fixed to said separation capillary.

16. The detector of claim 7 wherein said second guide tube is fixed to said working electrode.

17. A method of disposing a cylindrical electrode into the end of a capillary tube comprising the steps of:
   telescopically centralizing said cylindrical electrode within a first guide tube;
   telescopically centralizing said capillary tube within a second guide tube;

telescopically disposing said first and second guide tubes within an outer sleeve; and disposing said first and second guide tubes telescopically within said outer sleeve to insert said cylindrical electrode within said capillary tube by a predetermined distance.

18. The method of claim 17 wherein said first guide tube is a glass capillary tube and said step of telescopically centralizing said cylindrical electrode within said first guide tube comprises the step of heating and drawing down said capillary tube around said cylindrical electrode.

19. The method of claim 17 where said second guide tube is glass capillary tube and said step of telescopically centralizing said capillary tube within said second guide tube comprises the steps of drawing said second guide tube into a narrow capillary tip and breaking said narrow capillary tip at a position where the inner diameter of said narrow capillary tip provides a slip-fit for said capillary tube.

20. The method of claim 17 further comprising the step of fixing said capillary tube and cylindrical electrode to said first and second guide tubes respectively prior to said step of disposing said cylindrical electrode within said capillary tube by a predetermined distance.

* * * * *